United States Patent
Hatakeyama

(10) Patent No.: US 10,398,356 B2
(45) Date of Patent: Sep. 3, 2019

(54) SLEEPINESS DETECTING DEVICE

(71) Applicant: TOYOTA JIDOSHA KABUSHIKI KAISHA, Toyota-shi (JP)

(72) Inventor: Yoshiyuki Hatakeyama, Fuji (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 0 days.

(21) Appl. No.: 15/015,538

(22) Filed: Feb. 4, 2016

(65) Prior Publication Data
US 2016/0235343 A1 Aug. 18, 2016

(30) Foreign Application Priority Data
Feb. 12, 2015 (JP) ................. 2015-025886

(51) Int. Cl.
*A61B 5/11* (2006.01)
*A61B 5/00* (2006.01)

(52) U.S. Cl.
CPC .......... *A61B 5/1103* (2013.01); *A61B 5/1128* (2013.01); *A61B 5/4809* (2013.01); *A61B 5/0077* (2013.01)

(58) Field of Classification Search
CPC ............ A61B 2562/0219; A61B 3/113; A61B 5/7264; A61B 5/7275; A61B 5/1118; A61B 5/18; A61B 5/7282; A61B 5/4806; A61B 5/4809; A61B 5/4812; A61B 5/4815; A61B 5/6821; A61B 3/00; A61B 3/10; A61B 3/14; A61B 3/145; A61B 3/18; A61B 5/0245; A61B 5/05; A61B 5/486; G06F 3/013; G06F 19/3487; G06F 19/345;
(Continued)

(56) References Cited

U.S. PATENT DOCUMENTS 8,314,707 B2 * 11/2012 Kobetski ................. A61B 5/18
340/575
8,576,081 B2 11/2013 Hatakeyama et al.
(Continued)

FOREIGN PATENT DOCUMENTS

JP 7-241283 A 9/1995
JP 2007-236488 9/2007
(Continued)

*Primary Examiner* — Deborah L Malamud
(74) *Attorney, Agent, or Firm* — Oblon, McClelland, Maier & Neustadt, L.L.P.

(57) ABSTRACT

There is provided a device which detects sleepiness of a human being based on the opening and closing motion of an eyelid, in which an occurrence of sleepiness of a subject is detectable with accuracy more sufficient than before even for a subject who keeps from blinking intentionally when sleepiness increases. The inventive sleepiness detecting device comprises an eyelid state detector, detecting an opened/closed state of an eyelid of a subject; a transition time interval detector, detecting sequentially a time interval between transitions between an opened state and a closed state of the eyelid; an eyelid characteristic amount computer, computing an eyelid opening/closing characteristic amount from time series data of the time intervals; a sleepiness judging device, judging that the subject feels sleepiness when the eyelid opening/closing characteristic value falls below a first threshold value or exceeds beyond a second threshold value higher than the first threshold value.

12 Claims, 7 Drawing Sheets

Figure 1A:
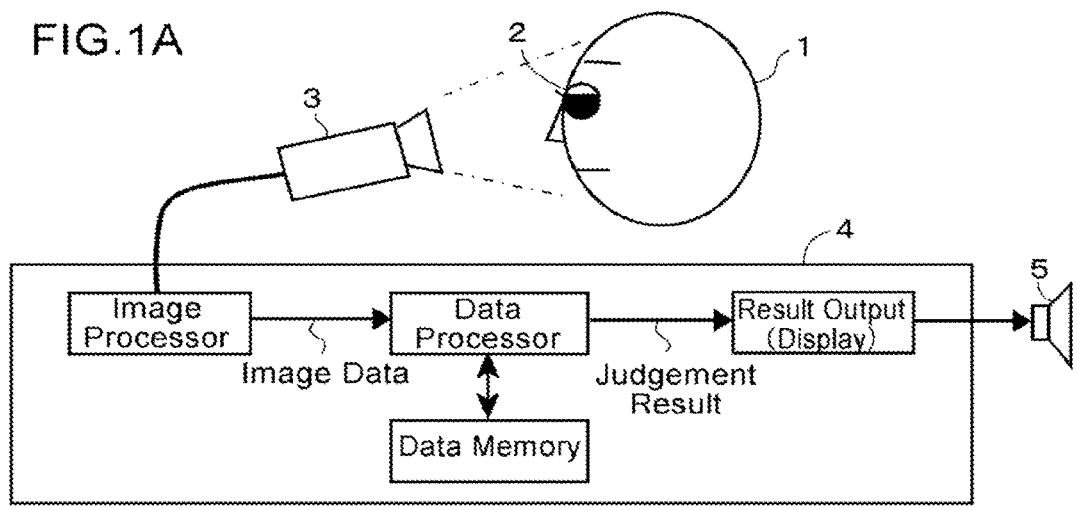

(58) Field of Classification Search
CPC ............ G06F 19/3418; G02B 27/0093; G06K 9/00845; G06K 9/00335; G06K 9/00281; B60K 28/06; B60W 40/08; B60W 2040/0872; B60W 2040/0818
See application file for complete search history.

(56) References Cited

U.S. PATENT DOCUMENTS

| | | |
|---|---|---|
| 8,823,792 B2 | 9/2014 | Omi |
| 2013/0215390 A1* | 8/2013 | Johns .................... A61B 3/113 351/209 |

FOREIGN PATENT DOCUMENTS

| | | |
|---|---|---|
| JP | 2009-261516 A | 11/2009 |
| JP | 2010-128649 A | 6/2010 |
| JP | 2011-167398 | 9/2011 |
| JP | 2013-202273 A | 10/2013 |
| WO | WO 2010/092860 A1 | 8/2010 |

* cited by examiner

SLEEPINESS DETECTING DEVICE

TECHNICAL FIELD

This invention relates to a device which detects sleepiness of a human being, and more specifically to a device which detects sleepiness (the occurrence of sleepiness) based on an index value obtained from the opening and closing motions of an eyelid of a human being. This inventive device is used, for example in order to detect the sleepiness of a driver during driving a vehicle or a mobile body.

BACKGROUND ART

As a device which detects sleepiness of a human being, there have been proposed a variety of devices judging if a person feels sleepiness by capturing an image of a face or an eyelid of the person and catching a motion of the eyelid and/or other variations in the facial expression in the captured image. For instance, patent document 1 proposes a structure, in which the length of a time in which an eyelid is continuously opened (hereafter, referred to as "eye opened time") is measured in captured images of an eye and its circumferential area of a subject being tested; the dispersion in the eye opened time (the standard deviation) is computed; and when the standard deviation of the eye opened time falls below a predetermined threshold value together with an increase in sleepiness, "a nap occurred" is judged. Further, in patent document 2, there has been proposed a structure in which occurrences of four sorts of facial expressions, including mouth motions in sighing, yawning, opening eyes widely and frowning, are measured from images of a subject's face, and an awakening degree, defined corresponding to an occurrence frequency of a combination of two of different sorts of the facial expressions, is outputted as an estimated result.

PRIOR TECHNICAL DOCUMENTS

Patent Documents

Patent document 1: JP2011-167398
Patent document 2: JP2007-236488

SUMMARY OF INVENTION

Technical Problem

By the way, in detecting sleepiness of a subject (human being) with a device as described above, the way of moving an eyelid and the variation of a facial expression when one feels a sleepiness differ depending upon subjects. For instance, generally, when a subject feels sleepiness, the motion of his/her eyelids becomes slow. However, in some cases, a subject blinks violently or opens eyes wide intentionally in order to prevent eyelids from closing together with the increase of sleepiness. In such a case, the standard deviation of the subject's eye opened time increases, and thus, in the structure of patent document 1, the eye opened time standard deviation will not become lower than a threshold value, so that it is difficult to detect sleepiness even if the subject feels it. Also in the structure of patent document 2, there could occur a variation, different than usual, in a facial expression in an increase of sleepiness, and thus, there could happen a case that an awaking degree could not be estimated correctly because of the occurrence of a condition in which the correspondences of a facial expression to any awaking degree has not been defined (Furthermore, in the structure of patent document 2, it is necessary to detect four or two facial expressions.). That is, there is room for improvement in a sleepiness detecting device in order to improve its performance.

Thus, for one of improvements in performances of a sleepiness detecting device as described above, one object of the present invention is to make it possible to detect an occurrence of sleepiness of a subject with accuracy more sufficient than before even in a case of a subject who blinks more violently intentionally, opens eyes wider or makes opening and closing motions of eyes more vigorous than usual in order to prevent from closing eyelids, instead of the opening and closing movement of eyelids being slow, in the increase of the sleepiness.

Solution to Problem

According to the present invention, the above-mentioned object is achieved by a sleepiness detecting device, comprising: an eyelid state detector which detects an opened/closed state of an eyelid of a subject; a transition time interval detector which detects sequentially a time interval between transitions between an opened state and a closed state of the eyelid; an eyelid characteristic amount computer which computes an eyelid opening/closing characteristic amount from time series data of the time intervals between transitions between an opened state and a closed state of the eyelid; a sleepiness judging device for judging that the subject feels sleepiness either when the eyelid opening/closing characteristic amount falls below a first threshold value or when the eyelid opening/closing characteristic amount exceeds beyond a second threshold value higher than the first threshold value.

In the above-mentioned structure, the "eyelid state detector" may be an arbitrary device which can judge whether an eyelid of a subject is opened or closed, and typically, there may be employed a device which judges the opened/closed state of an eyelid based on an image of the subject's eyelid captured (photographed) by a camera. Alternatively, the eyelid state detector may be a device which judges the opened/closed state of an eyelid based on an ocular potential signal of the subject. The "time interval between transitions between an opened state and a closed state of the eyelid" is an interval between time points at which a transition in an eyelid from an opened state to a closed state or from a closed state to an opened state occurs in the data of judgment results of whether the eyelid is opened or closed obtained in time series by the eyelid state detector. Concretely, this time interval may be: (1) a time interval from a transition of an eyelid from its closed state to its opened state to a transition of the eyelid from its opened state to its closed state, namely, a time length in which the eyelid is continuously opened (eye opened time); (2) a time interval from a transition of an eyelid from its opened state to its closed state to the next transition from its opened state to its closed state, namely, a time length from when an eyelid is closed until it is closed again after it is once opened (a blink start time interval); (3) a time interval from a transition of an eyelid from its closed state to its opened state to the next transition of from its closed state to its opened state, namely, a time length from when an eyelid is opened until it is opened again after it is once closed (a blink end time interval); or (4) a time interval from a transition of an eyelid from its opened state to its closed state to a transition of the eyelid from its closed state to its opened state, namely, a time length in which the eyelid is continuously closed (eye closed time). And, the "eyelid opening/closing characteristic amount" is, briefly speaking, an amount which correlates with the presence or absence, or the degree, of sleepiness of the subject, extracted from the above-mentioned "time interval between transitions between the opened state and closed state of an eyelid". Concretely, when a subject feels sleepiness, the "time interval between transitions between the opened state and closed state of an eyelid" statistically changes in comparison with when the subject does not feel sleepiness, and thus, for such a "eyelid opening/closing characteristic amount", there may be employed, for example, an index value indicating a statistical amount, and more specifically, a standard deviation, an average value, a median value, variance value, etc., of the "time interval between transitions between the opened state and closed state of an eyelid" may be employed. Especially, when a subject feels sleepiness, the opening and closing motions of the eyelid become slower or more vigorous than in usual conditions in the absence of sleepiness, so that its statistical variation will change. Thus, in that case, the standard deviation or variance value of the "time interval of the transition between the opened state and closed state of an eyelid" can be preferably employed for the "eyelid opening/closing characteristic amount".

Further, in the case of the above-mentioned inventive device, either when the eyelid opening/closing characteristic amount falls below a first threshold value or when the eyelid opening/closing characteristic amount exceeds beyond a second threshold value higher than the first threshold value, i.e., in both of the cases, it is judged that the subject feels sleepiness. Namely, when the eyelid opening/closing characteristic amount deviates from between the first threshold value and the second threshold value, a judgment that the subject feels sleepiness is made. As already noted, when a person feels sleepiness, a change appears in the opening and closing motion of an eyelid, and typically, the motion of the eyelid becomes slower and the value of "the time interval of the transitions between the opened state and closed state of the eyelid" and/or its variation decrease statistically in many cases. However, in some persons, when they feel sleepiness, any intentional motion of an eyelid to bear the sleepiness, such as opening eyes wide intentionally, blinking vigorously, could be made, and thus, in the cases of such subjects, the value and/or variation of "the time interval of the transition between the opened state and closed state of the eyelid" increase. Thus, in the inventive device, the threshold value for the eyelid opening/closing characteristic amount is set not only in the lower side but also in the higher side than its normal value in the absence of feeling sleepiness. Thereby, in a case of a subject whose time interval between transitions between the opened state and closed state of an eyelid or its variation increase, it is expected to more certainly achieve the judgment of sleepiness.

Further, with respect to the above-mentioned judgment of the presence or absence of sleepiness, there are individual variations and intraindividual variations in the time intervals of transitions between the opened state and closed state of an eyelid when a subject feels no sleepiness and when a subject feels sleepiness. Accordingly, preferably, the first and second threshold values to be used for the references in judging the presence or absence of sleepiness for a certain subject are determined with time intervals of transitions between the opened state and closed state of an eyelid of the certain subject (in the period relatively close to the time of conducting the judgment of sleepiness). Thus, in the structure of the present invention, the first and second threshold values may be determined based on eyelid opening/closing characteristic amounts in a predetermined period before the time of the judgment of sleepiness. When the inventive device is used in order to judge the presence or absence of sleepiness of a driver of a vehicle, the predetermined period before the time of the judgment of sleepiness may be, for example, a predetermined period from a running start of the vehicle until statistically significant data volume can be obtained. Further, for the first and second threshold values, concretely, for example, there may be employed values obtained by multiplying a predetermined positive number smaller than 1 and a predetermined positive number larger than 1 to the average value of eyelid opening/closing characteristic amounts in a predetermined period before a time of a judgment of sleepiness, respectively. According to this structure, since the references for judgment of sleepiness will be set using data of the subject to be judged for sleepiness in the time relatively close to the judgment, it is expected that influences on the result due to individual and intraindividual variations in time intervals of transitions between the opened state and closed state of an eyelid will be suppressed.

Effect of Invention

Thus, in the above-mentioned structure of the present invention, when the eyelid opening/closing characteristic amount, i.e., an index value of whether or not a subject feels sleepiness deviates from the range between the first threshold value and the second threshold value, a judgment that the subject feels sleepiness is made, and therefore, when the opening and closing motion of an eyelid, measured with the time interval of the transitions between the opened state and closed state of the eyelid, differs from the conditions when a subject does not feel sleepiness, namely, either when the opening and closing motion of the eyelid becomes more moderate or more vigorous than in the conditions when a subject does not feel sleepiness, a judgment that the subject feels sleepiness can be made. According to this structure of the present invention, not only for a subject of whom the motion of an eyelid becomes slow in feeling sleepiness, but also for a subject of whom the motion of an eyelid becomes vigorous in feeling sleepiness, the sleepiness can be more surely detected than ever. Moreover, according to the structure of the present invention, only the information on the opening and closing condition of an eyelid is required as the information measured from a subject and necessary to detect its sleepiness, and therefore, it is advantageous in that the structure of the device becomes simpler than those using information obtained by two or more measurements.

Other purposes and advantages of the present inventions will become clear by explanations of the following preferable embodiments of the present invention.

BRIEF DESCRIPTIONS OF DRAWINGS

Figure 1B:
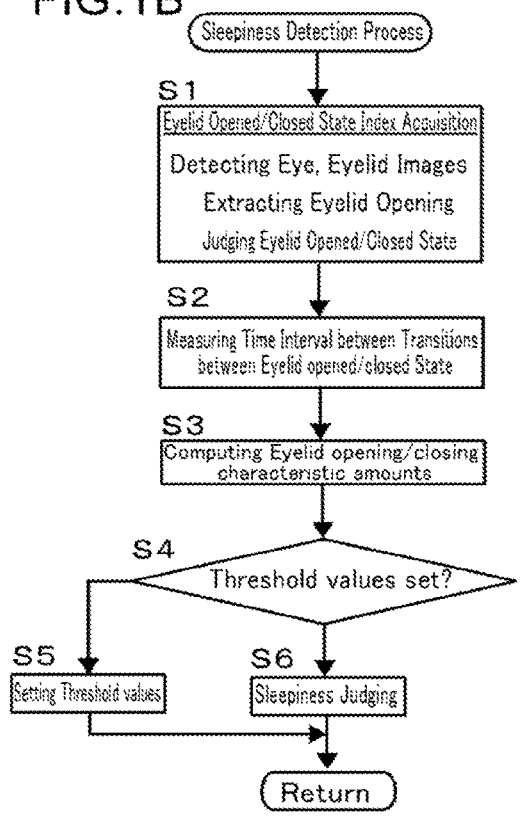

FIG. 1A schematically shows the structure of an embodiment of a sleepiness detecting device according to the present invention, and FIG. 1B shows an overview of the operations of the embodiment of the sleepiness detecting device according to the present invention in the form of a flow chart.

Figure 2A:
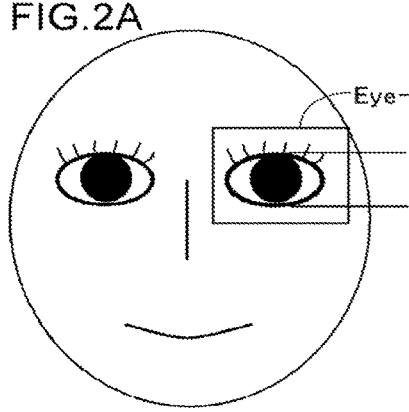
Figure 2B:
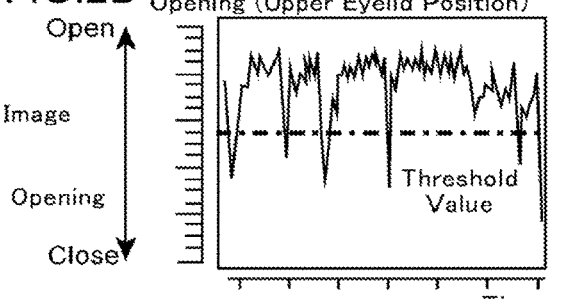
Figure 2C:
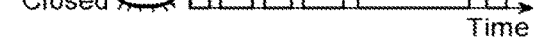
Figure 2C:
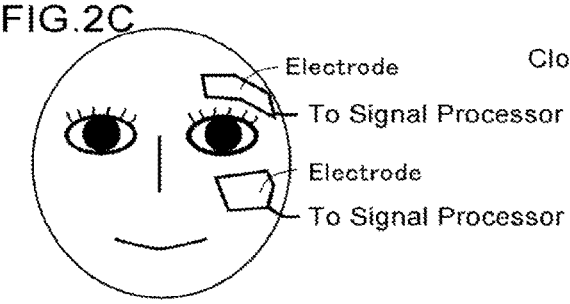

FIG. 2A shows a schematic diagram of a subject's face of in capturing an image of an eye and an eyelid with a camera in the inventive sleepiness detecting device. FIG. 2B shows an example of a time variation of an opening of an eyelid obtained from images of the eyelid, and an example of a time variation in the eyelid opened/closed state index value obtained by binarizing the opening of the eyelid. FIG. 2C shows schematically an arrangement of electrodes attached to a subject's face, when the opening of an eyelid is detected with an ocular potential signal in the inventive sleepiness detecting device.

Figure 3A:
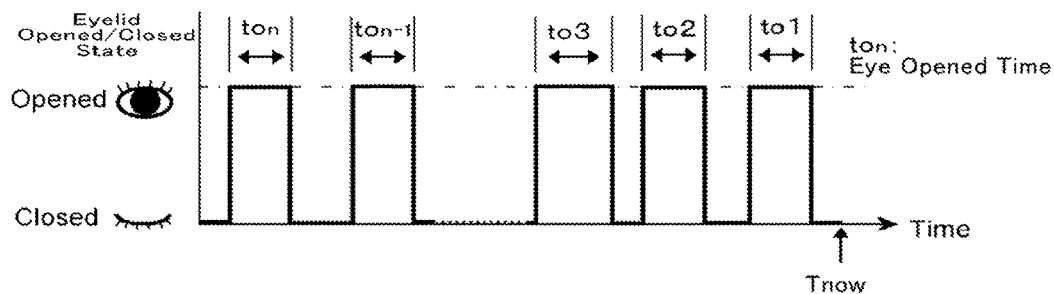
Figure 3B:
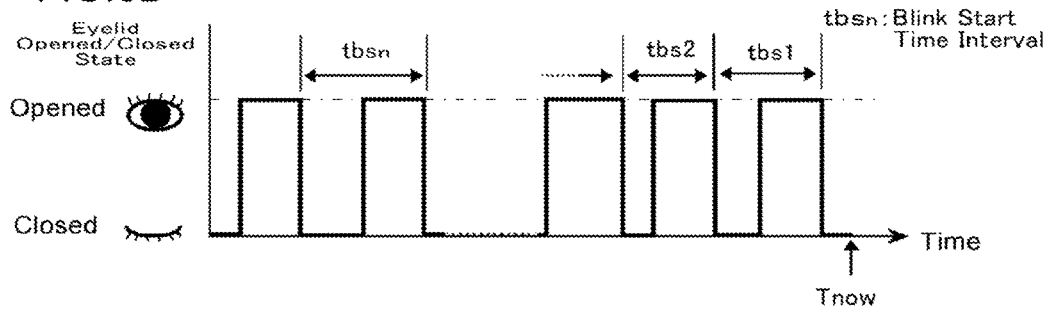
Figure 3C:
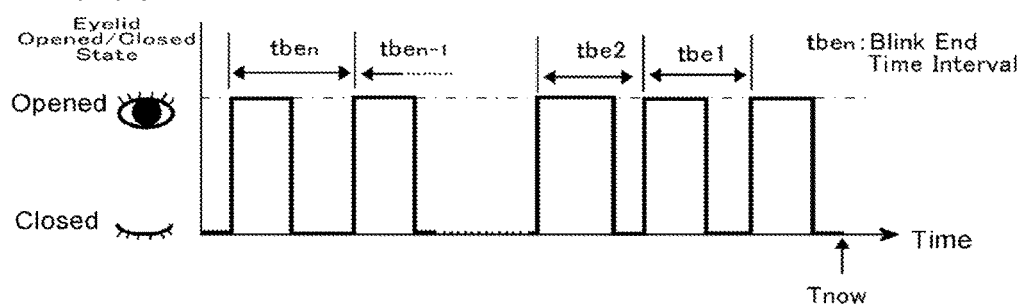

FIG. 3A is a drawing explaining about an "eye opened time" measured in time series data of eyelid opened/closed state index value. FIG. 3B is a drawing explaining about a "blink start interval" measured in time series data of eyelid opened/closed state index value. FIG. 3C is a drawing explaining about a "blink end interval" measured in time series data of eyelid opened/closed state index value.

Figure 4A:
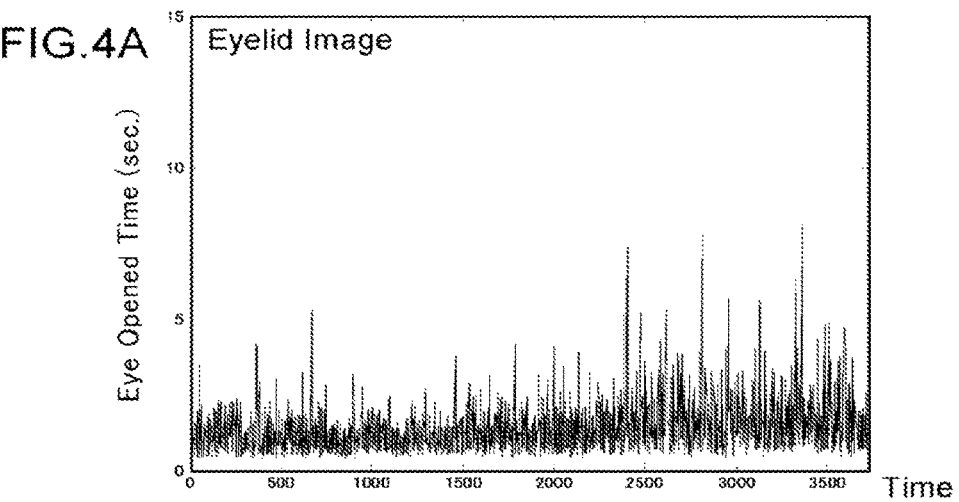
Figure 4B:
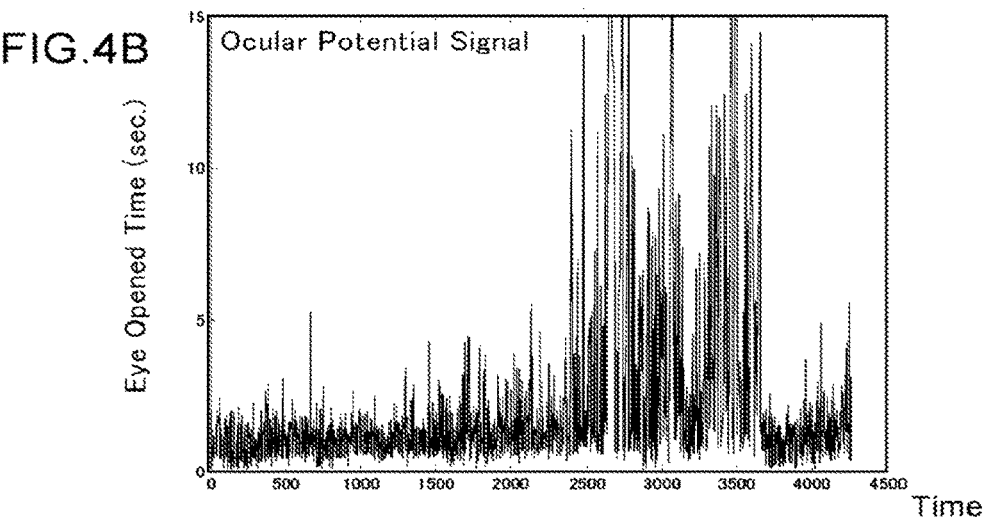
Figure 4C:
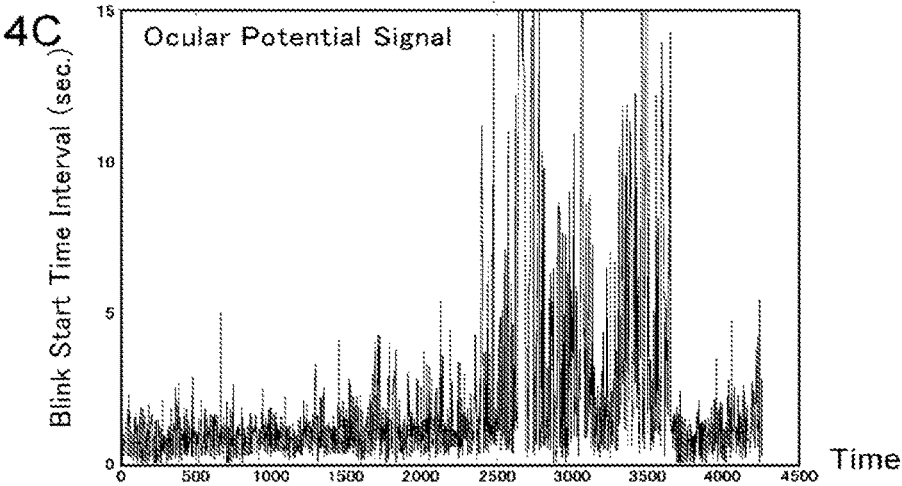

FIG. 4A shows an example of time series data of eye opened time, measured in eyelid opened/closed state index values obtained from time variation of the opening of an eyelid obtained from images of an eye and an eyelid. FIG. 4B shows an example of time series data of eye opened time measured in eyelid opened/closed state index values obtained from time variation of the opening of an eyelid obtained from ocular potential signals. FIG. 4C shows an example of time series data of blink start time measured in eyelid opened/closed state index values obtained from time variation of the opening of an eyelid obtained from ocular potential signals.

Figure 5A:
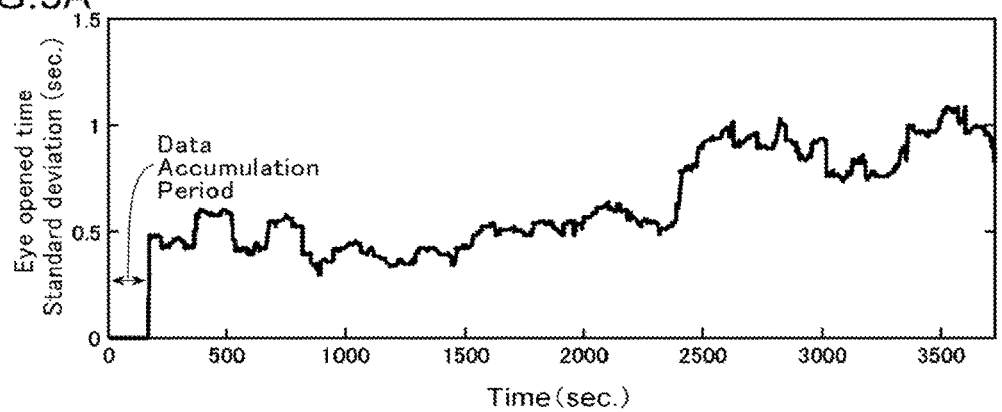
Figure 5B:
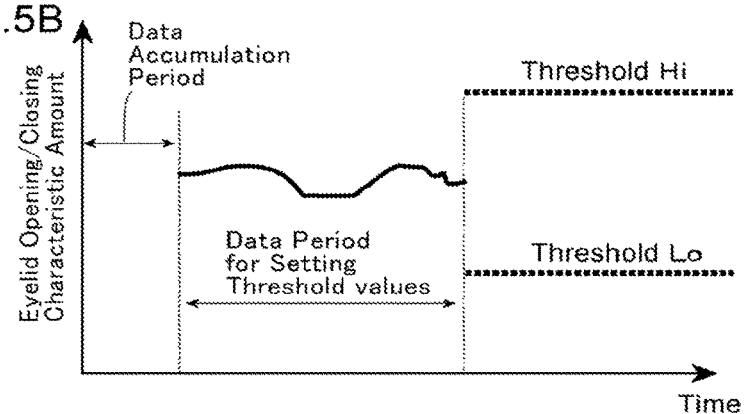

FIG. 5A shows an example of time series data of standard deviation of eye opened time computed from the time series data of the eye opened time of FIG. 4A. FIG. 5B explains about a setting method of threshold values for eyelid opening/closing characteristic amount.

Figure 6A:
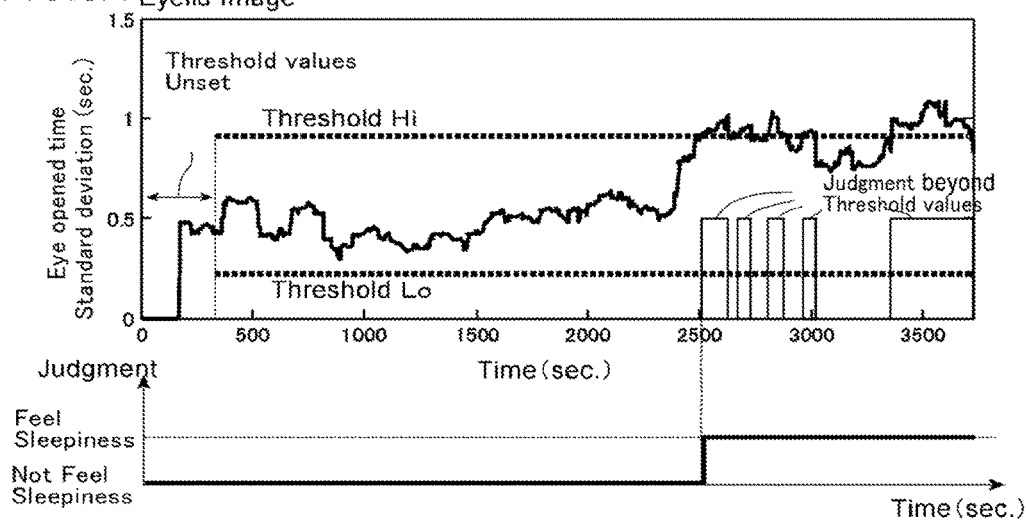
Figure 6B:
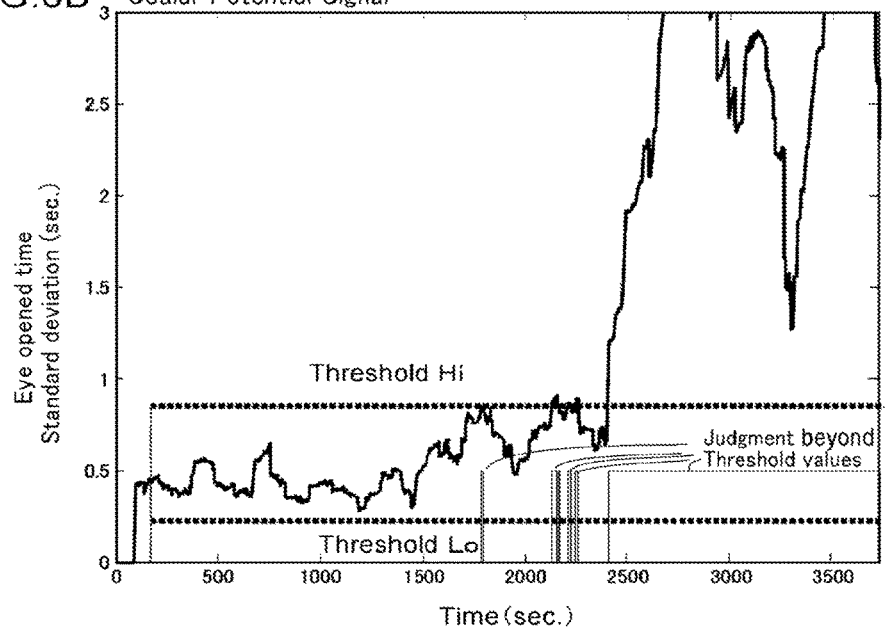

FIG. 6A shows an example of judging sleepiness in time series data of standard deviation of eye opened time, computed from the time series data of the eye opened time obtained from eyelid images of FIG. 4A. FIG. 6B shows an example of judging sleepiness in time series data of standard deviation of eye opened time, computed from the time series data of the eye opened time obtained from the ocular potential signals of FIG. 4B.

Figure 7A:
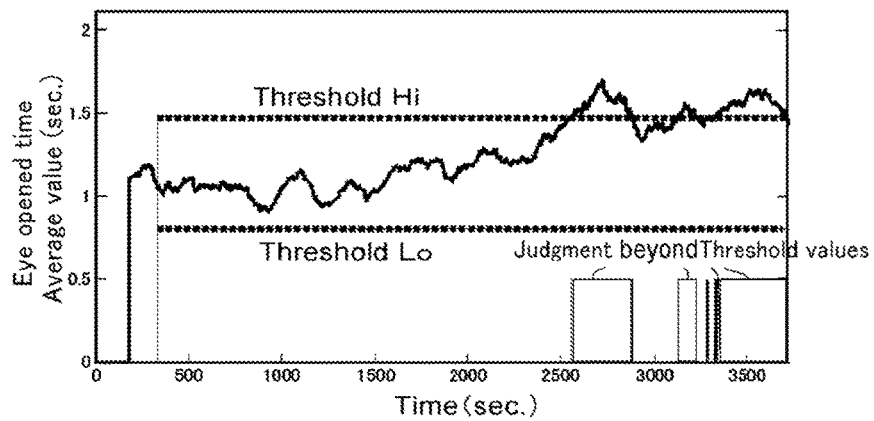
Figure 7B:
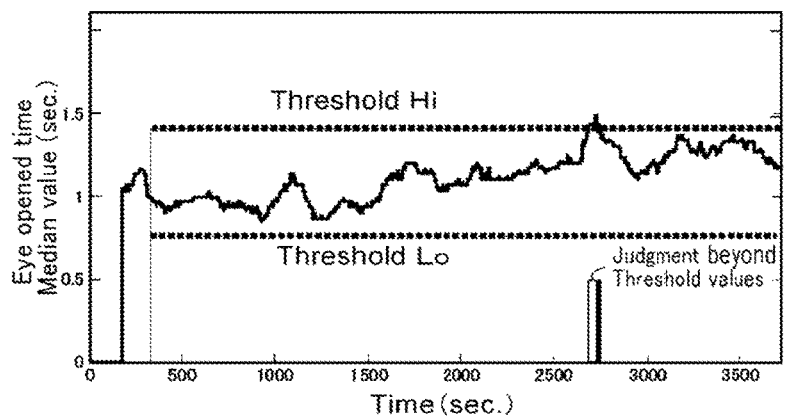
Figure 7C:
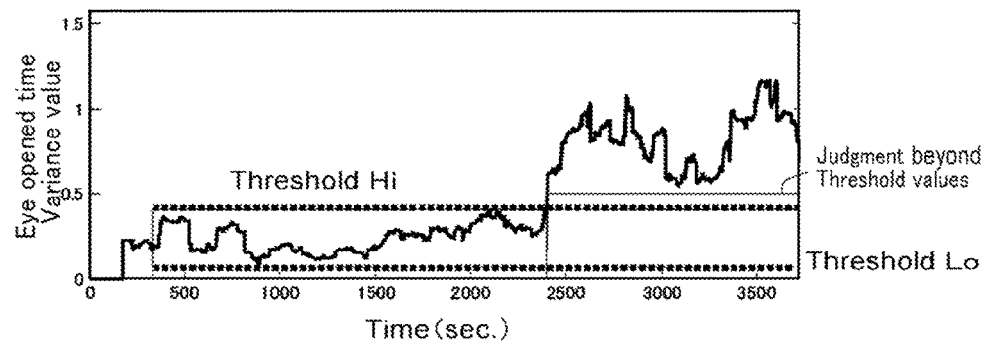

FIGS. 7A, 7B and 7C are drawings similar to FIG. 6A, showing examples, using, for eyelid opening/closing characteristic amount for judging sleepiness, the average value, median value and variance value of eye opened time, respectively.

EXPLANATIONS OF REFERENCE NUMERALS

1—Subject
2—Eye of a subject
3—Camera
4—Signal processing device

DESCRIPTION OF EMBODIMENTS

In the followings, preferable embodiments of the present invention are described in detail.

Structure of Device

Briefly, the sleepiness detecting device in accordance with the present invention is a device of a type which measures opening and closing motions of an eyelid of a subject, extracts eyelid opening/closing characteristic amounts having a correlation with the subject's sleepiness from time series data of the measured opening and closing motions of the eyelid, and judges that the subject feels sleepiness when the eyelid opening/closing characteristic amount enters into a range in which the subject feels sleepiness, similarly to patent document 1. Referring to FIG. 1A, in the basic structure of the inventive sleepiness detecting device, first, an image capturing device, such as a camera 3, is set so that an eye and an eyelid 2 of a subject 1 will be covered in the field of view of the image capturing device, and image signals acquired with the image capturing device are taken into a signal processing device 4. In this regard, as mentioned later, the opening and closing motion of the eye and eyelid 2 of the subject 1 may be detected with ocular potential signals, and in that case, the signals from electrodes applied on the subject's face are given to the signal processing device 4. Then, in the signal processing device 4, an image processing portion generates an image including the image of the eye and eyelid 2 of the subject 1 from the image signals sent from the image capturing device. Then, using the images of the eye and eyelid 2 of the subject, a data processing portion performs data processing necessary for detection of sleepiness of the subject and a judgment of the presence or absence of sleepiness, as described later. Thus, when a judgment that the subject feels sleepiness is made in the data processing portion, the judgment result is transmitted to a result output portion, where, for instance, the result is informed to the subject through sound with a speaker 5, a physical stimulus given to the subject by a vibrator giving, etc. The signal processing devices 4 may be, typically, a computer device, equipped with a CPU, memories, input/output device (I/O), etc. mutually connected with bidirectional common bus (not illustrated) in a usual manner, and operations of the respective portions of the sleepiness detecting device are achieved by executing computer programs in CPU.

Overview of Operations of Device

Referring to FIG. 1B, in the processes of detecting sleepiness by the inventive device, according to the programs, first, the index value indicating the opened/closed state of an eyelid of a subject is sequentially acquired (step 1), and, in the time series data of the index values, a time interval between transitions between the opened state and closed state of the eyelid is sequentially measured (step 2), and next, the "eyelid opening/closing characteristic amount" having correlation with the presence or absence of sleepiness in the time series data of the time intervals of transitions between the opened state and closed state of the eyelid is sequentially computed (step 3). Then, before setting the threshold values for the "eyelid opening/closing characteristic amount" for the judgment of the presence or absence of sleepiness (usually, in a predetermined period from just after starting the use of the device), processes for the setting of the threshold values are executed (steps 4 and 5). Thus, when the threshold values are set after the repeating of the cycle in a predetermined period as described later (step 4), the judgment of sleepiness of the subject will be conducted (step 6). Namely, the eyelid state detector, the transition time interval detector, the eyelid characteristic amount computer and the sleepiness judging device each are realized by the image capturing device (or electrode device) in FIG. 1A and the operations of the signal processing device 4 according to programs. In the followings, each process in the above-mentioned series is explained in detail.

Acquisition of Eyelid Opened/Closed State Index Value (Step 1)

In the acquisition of index values indicating opened/closed state of an eyelid of a subject (eyelid opened/closed state index value) in the inventive device, in one manner, as noted, the opening and closing motions of an eyelid are detected in images of an eye and an eyelid of a subject sequentially captured with an image capturing device such as a camera, and there is prepared time series data indicating a state that the eyelid is opened and a state that the eyelid is closed from the detected data of the opening and closing motions of the eyelid. In that case, first, the image capturing device, such as a camera etc. may be installed on an arbitrary place so that the field of view may cover the subject's eye and eyelid, as schematically drawn in FIG. 2A. For instance, in a case of judging sleepiness of a driver of a vehicle, a concrete position of an image capturing device, such as camera etc., may be set to an arbitrary place, as long as the image of the subject's eye and eyelid can be captured, such as on the dashboard of a vehicle, a handle, a ceiling, etc. Also, the image capturing device, such as a camera etc., may be attached to any subject's wearing article, such as glasses, a hat, etc. The image capturing device, such as a camera, etc., sequentially takes photographs of the subject's eye and eyelid and outputs image signals, from which the images of the eye and eyelid are formed sequentially.

When the successive or continuous images of the subject's eye and eyelid are obtained, the positions of an upper eyelid and a lower eyelid are sequentially detected in the images and the distances between the upper and lower eyelids are measured, and thereby, time series data of an opening of the eyelid (the distance between the upper and lower eyelids) is prepared as drawn in FIG. 2B, the upper row. The detection of the positions of an upper eyelid and a lower eyelid in an image may be done by an arbitrary image processing method based on properties in brightness or hue of images of the upper and lower eyelids or the image of an eyeball. And the obtained time series data of the opening of the eyelid is binarized into an opened state and a closed state by judging whether or not each data value exceeds beyond a threshold value which is set to the boundary of the opened state and the closed state of the eyelid between the maximum and the minimum of the eyelid opening, and thereby, there is prepared time series data of the eyelid opened/closed state index value, which is an index value indicating whether or not the eyelid is opened or closed, as drawn in FIG. 2B, the lower row.

The eyelid opening may be measured in any other manner, and it should be understood that such a case belongs to the scope of the present invention, also. Alternatively, as already noted, for example, the eyelid opening can be measured with the height of an ocular potential signal of a subject (voltage change owing to the rotation of the eyeball accompanying blinking). In that case, as schematically drawn in FIG. 2C, for example, plural electrodes each are applied on plural regions, such as the upper and lower sides of a subject's eye, and the voltage between the electrodes is measured as a signal (ocular potential signal), and transmitted to the signal processing device. Further, electrodes may be attached to any head wearing article, such as glasses, goggles, a helmet, or may be built in any accessory, such as a tattoo applied on skin. Also in the case of the ocular potential signal, time series data similar to that in FIG. 2B are obtained for the motions of an eyelid, and thus, by binarizing that data, time series data of eyelid opened/closed state index values will be prepared.

In this regard, as explained later, since calculation processes of a statistical quantity of the eyelid opened/closed state index value over a certain period is conducted in the process of the inventive device, the time series data of eyelid opened/closed state index values are memorized by the data memory in the signal processing device 4.

Computation of Eyelid Opening/Closing Characteristic Amount (Steps 2 and 3)

When time series data of eyelid opened/closed state index value is obtained, an amount which has correlation with the presence or absence of a subject's sleepiness is extracted from the time series data of the eyelid opened/closed state index values. In the present invention, this amount which has correlation with the presence or absence of a subject's sleepiness is referred to as an "eyelid opening/closing characteristic amount". In this embodiment, the "eyelid opening/closing characteristic amount" is computed out by measuring sequentially time intervals between transitions of the eyelid opened/closed state in the time series data of eyelid opened/closed state index values in a predetermined period and processing statistical calculations of the measured transition time intervals. In the followings, the computation process of the "eyelid opening/closing characteristic amount" is explained.

(i) Measurement of Time Interval between Transitions of Eyelid Opened/Closed State (Step 2)

In the computation process of eyelid opening/closing characteristic amount, first, a time interval between transitions between the opened state and closed state of an eyelid is measured in the time series data of the eyelid opened/closed state index values memorized in data memory. As described in the column of "Summary of Invention", the time interval between transitions between the opened state and closed state of an eyelid (Hereinafter, referred to as "eyelid opened/closed state transition time interval") is the interval between time points of occurrences of transitions of an eyelid from the opened state to the closed state or from the closed state to the opened state. Concretely, the "eyelid opened/closed state transition time interval" may be: (1) Eye opened time (a time length in which an eyelid is continuously opened), i.e., a time interval from a transition of an eyelid from its closed state to its opened state to a transition of the eyelid from its opened state to its closed state (FIG. 3A); (2) Blink start time interval (a time length from when an eyelid is closed until it is closed again after it is once opened), i.e., a time interval from a transition of an eyelid from its opened state to its closed state to the next transition from its opened state to its closed state (FIG. 3B); (3) Blink end time interval (a time length from when an eyelid is opened until it is opened again after it is once closed), i.e. a time interval from a transition of an eyelid from its closed state to its opened state to the next transition of from its closed state to its opened state (FIG. 3C); and (4) Eye closed time (a time length in which an eyelid is continuously closed), i.e., a time interval from a transition of an eyelid from its opened state to its closed state to a transition of the eyelid from its closed state to its opened state. Further, in either of the cases (1)-(4), the time series data of values of time intervals of transitions are prepared by measuring the eyelid opened/closed state transition time interval while tracing back to the past from the present (Tnow) as drawn in FIG. 3A-FIG. 3C. For example, in the case of eye opened time in FIG. 3A, time series data is constituted by measuring the eye opened times $t_{on}$ while tracing back from the present time Tnow as $to_1, to_2, to_3, ---, to_{n-1}, to_n$. FIGS. 4A, 4B and 4C each show examples of time series data of eye opened times, measured in eyelid opened/closed state index values obtained from time variations of the opening of an eyelid obtained from images of an eye and an eyelid; eye opened times, measured in eyelid opened/closed state index values obtained from time variations of the opening of an eyelid obtained from ocular potential signals; and blink start time interval, measured in eyelid opened/closed state index values obtained from time variations of the opening of an eyelid obtained from ocular potential signals.

(ii) Computation of Eyelid Opening/Closing Characteristic Amount (Step 3)

As noted above, when the eyelid opened/closed state transition time intervals have been measured, a statistic amount of the eyelid opened/closed state transition time intervals is computed as an eyelid opening/closing characteristic amount, using an arbitrary number of the data while tracing back along the time-axis from the present or judgment point. For the statistic amount, there may be employed the standard deviation value, the variance value, the average value, the median value, etc. Concretely, for example, in a case that the eye opened time is chosen as the eyelid opened/closed state transition time interval and the standard deviation value of the eye opened time is chosen as the eyelid opening/closing characteristic amount, while tracing back from the present time point, n of eye opened time data:

$$\{to_1, to_2, to_3, to_{n-1}, to_n\} \quad (1)$$

are extracted from data memory, and the standard deviation value SD (t) is computed by $$SD(t) = \sqrt{\frac{1}{n}\sum_{i=1}^{n}(toi-toa)^2} \quad (2)$$

Here, n is the number of extracted data points; i is the data number, toi is the i-th eye opened time data, and toa is the average value of n of the extracted data values. And the standard deviation value (eyelid opening/closing characteristic amount) SD (t) is sequentially computed as shown in FIG. 5A during repeating the cycle of FIG. 1B. In this regard, referring to the drawing, in a certain period from the start of the process (data accumulation period), since the number of data points has not reached to the number required for computing a statistically significant eyelid opening/closing characteristic amount, the eyelid opening/closing characteristic amount is not computed. It will be understood that, also in the cases of selecting the variance value, the average value or the median value of blink start time intervals, blink end time intervals or eye closed times for the eyelid opening/closing characteristic amount, similarly, the eyelid opening/closing characteristic amount is computed in time series with an arbitrary number of data while tracing back along the time-axis from the present time point or the judgment time point.

Setting of Threshold Valued (Steps 4 and 5)

In the present invention, as already noted, when the above-mentioned eyelid opening/closing characteristic amount, such as the standard deviation value of eyelid opened/closed state transition time intervals, deviates from a range in which a subject does not feel sleepiness, a judgment that the subject feels sleepiness is made. Therefore, the setting of threshold values for defining the range of the eyelid opening/closing characteristic amount in which a subject does not feel sleepiness is performed. In this connection, as noted, it has been assumed so far that the eyelid opening/closing characteristic amount when a subject felt sleepiness always decreases as compared with when a subject does not feel sleepiness. However, it was found that, in some persons, the eyelid opening/closing characteristic amount increases when he/she feels sleepiness. Thus, in the inventive device, two threshold values are set at the lower limit (the first threshold value) and the upper limit (the second threshold value), corresponding to the boundaries of the range of eyelid opening/closing characteristic amount when a subject does not feel sleepiness. Further, since there are individual variations and intraindividual variations in the range of the eyelid opening/closing characteristic amount when a subject does not feel sleepiness, it is preferable that the threshold values defining the range are set up based upon eyelid opening/closing characteristic amount when the subject does not feel sleepiness in a period as close to the time of judging sleepiness as possible. Then, in this embodiment, as schematically drawn in FIG. 5B, the threshold values may be set using the eyelid opening/closing characteristic amount in a predetermined period just after the operation start of the inventive device. For example, in a case of using the inventive device for judging sleepiness of a driver (a subject) of a vehicle, the period for accumulating data for the setting of threshold values may be a predetermined period just after the running of the vehicle (The judgment of sleepiness is carried out under the condition that the threshold values have been set after lapse of the data period for setting the threshold values as illustrated).

In one manner of concrete processes for the setting of threshold values, the threshold value Hi (upper limit) and the threshold value Lo (lower limit) may be computed using M of eyelid opening/closing characteristic amount data in a period for accumulating data for setting the threshold values by:

$$\text{Threshold value Hi} = Thh \times Mav \quad (3a)$$

$$\text{Threshold value Lo} = Thl \times Mav \quad (3b)$$

Here, Thh is a positive coefficient larger than one, and Thl is a positive coefficient smaller than one. Mav is the average value of the M of eyelid opening/closing characteristic amounts. M, Thh, and Thl may be determined experimentally. According to the expressions (3a) and (3b), since the threshold values will be set with the average value of the M of eyelid opening/closing characteristic amounts of the same subject in the data period for setting threshold values in a period relatively close to the time of a judgment, it is expected that influences of individual variations or intraindividual variations in eyelid opening/closing characteristic amounts can be suppressed.

In the process cycle of the device, after computing an eyelid opening/closing characteristic amount (step 3), when threshold values has not been set (step 4), the process of setting threshold values is performed (step 5). In this process, a cycle is repeated until M of eyelid opening/closing characteristic amounts have been accumulated, and when the number of eyelid opening/closing characteristic amounts reaches to M, upper and lower threshold values are computed and set with the above-mentioned expressions.

Judgment of the Presence or Absence of Sleepiness (Step 6)

Then, when the threshold values have been set up, the judgment of whether or not the eyelid opening/closing characteristic amount is within the range defined between the upper and lower threshold values is conducted, and when the eyelid opening/closing characteristic amount deviates from the range between the upper and lower threshold values, it is judged that the subject feels sleepiness. FIG. 6A shows an example of conducting a judgment of sleepiness in the time series data of the standard deviation of the eye opened time computed from the time series data of the eye opened time obtained from eyelid images in FIG. 4A, and in this illustrated example, it was judged that the subject felt sleepiness because the standard deviation exceeded beyond the threshold value Hi around 2500 seconds (In the illustrated example, the threshold values were computed by setting M=100, Thh=2.0, and Thl=0.5.). In this regard, as illustrated, the standard deviation value can repeat increasing and decreasing relative to the threshold value Hi. In this respect, when a deviation of the eyelid opening/closing characteristic amount from the range defined between the upper and lower threshold values is detected even once, after that, it may be judged that the subject feels sleepiness as shown in FIG. 6A lower row.

The judgment of sleepiness as illustrated in FIG. 6A can be similarly realized by using the standard deviation of eye opened times computed from time series data of the eye opened times obtained from ocular potential signals as illustrated in FIG. 6B. Moreover, FIGS. 7A, 7B and 7C each are examples of employing as the eyelid opening/closing characteristic amount the average value, the median value and the variance value of the eye opened time, respectively, and in those cases, the judgment of sleepiness was performable similarly.

Then, as noted above, when the sleepiness of the subject is detected, this may be informed to the subject with a loudspeaker or a vibrator, etc.

As described above, in the above-mentioned device in accordance with the present invention, when the eyelid opening/closing characteristic amount, which is an index value of whether or not a subject feels sleepiness, deviates from the range defined between the upper and lower threshold values, a judgment that the subject feels sleepiness is made. Thereby, sleepiness becomes detectable not only in a case of a subject whose eyelid opening/closing characteristic amount becomes lower when he/she feels sleepiness than in a usual condition, but also in a case of a subject whose eyelid opening/closing characteristic amount becomes higher when he/she feels sleepiness than in a usual condition.

Although the above explanation has been described with respect to embodiments of the present invention, it will be apparent for those skilled in the art that various modifications and changes are possible, and that the present invention is not limited to the above-illustrated embodiments and may be applied to various devices and apparatus without deviating from the concepts of the present invention.

The invention claimed is:

1. A sleepiness detecting device, comprising:
a signal processor configured to:
detect an opened/closed state of an eyelid of a subject;
measure sequentially time intervals from a first transition between a first opened state of the eyelid and a first closed state of the eyelid to a second transition between a second opened state of the eyelid and a second closed state of the eyelid, the measured time intervals including at least a time that the eyelid is open;
compute an eyelid opening/closing characteristic statistical amount from a plurality of data of the sequentially measured time intervals, the eyelid opening/closing characteristic statistical amount being a standard deviation of the measured time intervals:
judge that the subject feels sleepiness when the eyelid opening/closing characteristic statistical amount falls below a first threshold value;
judge that the subject feels sleepiness when the eyelid opening/closing characteristic statistical amount exceeds a second threshold value higher than the first threshold value; and
transmit a judgment result when it is judged that the subject feels sleepiness to a result output portion where the judgement result is informed to the subject.

2. The device of claim 1,
the first opened state and the second opened state are the same state,
the first transition being a transition of the eyelid from the first closed state to the first opened state, and
the second transition being a transition of the eyelid from the first opened state to the second closed state.

3. The device of claim 1,
the first transition being a transition of the eyelid from the first opened state to the first closed state, and
the second transition being transition of the eyelid from the second opened state to the second closed state.

4. The device of claim 1,
the first transition being a transition of the eyelid from the first closed state to the first opened state, and
the second transition being a transition of the eyelid from the second closed state to the second opened state.

5. The device of claim 1, the eyelid opening/closing characteristic statistical amount being an index value.

6. The device of claim 1, the first and the second threshold values being determined based on the eyelid opening/closing characteristic statistical amount in a predetermined period before a time of the judgment that the subject feels sleepiness.

7. The device of claim 6, the first and the second threshold values each being values obtained by multiplying a predetermined positive number smaller than 1 and a predetermined positive number larger than 1 to an average value of a plurality of the eyelid opening/closing characteristic statistical amounts in the predetermined period before the time of the judgment that the subject feels sleepiness.

8. The device of claim 1, the signal processor judging the opened/closed state based upon a camera image of the eyelid of the subject.

9. The device of claim 1, the signal processor judging the opened/closed state based on an ocular potential signal of the subject.

10. The device of claim 1, the result output portion informing the judgement result by sound.

11. The device of claim 1, the result output portion informing the judgement result by physical stimulus.

12. The device of claim 1, wherein the first and second threshold values correspond to boundaries of the range of the standard deviation of the measured time intervals set when a subject does not feel sleepiness.

* * * * *